(12) United States Patent
Jin Wong et al.

(10) Patent No.: US 10,908,085 B2
(45) Date of Patent: Feb. 2, 2021

(54) MODULAR ASSAY SYSTEM

(71) Applicant: MAST GROUP LIMITED, Liverpool (GB)

(72) Inventors: Ken Jin Wong, Liverpool (GB); David Hugh Williams, Liverpool (GB); Iain McElarney, North Somerset (GB); Elizabeth Gillies, Horwich (GB)

(73) Assignee: MAST GROUP LIMITED, Liverpool (GB)

( * ) Notice: Subject to any disclaimer, the term of this patent is extended or adjusted under 35 U.S.C. 154(b) by 0 days.

(21) Appl. No.: 14/761,048

(22) PCT Filed: Jan. 16, 2014

(86) PCT No.: PCT/GB2014/050124
§ 371 (c)(1),
(2) Date: Jul. 15, 2015

(87) PCT Pub. No.: WO2014/111719
PCT Pub. Date: Jul. 24, 2014

(65) Prior Publication Data
US 2015/0362431 A1    Dec. 17, 2015

(30) Foreign Application Priority Data

Jan. 16, 2013  (GB) .................................. 1300813.1

(51) Int. Cl.
*G01N 21/64* (2006.01)
*G01N 33/487* (2006.01)
(Continued)

(52) U.S. Cl.
CPC ........ *G01N 21/6428* (2013.01); *B01L 3/5027* (2013.01); *B01L 3/545* (2013.01);
(Continued)

(58) Field of Classification Search
CPC .......... G01N 2035/00326; G01N 2035/00821; G01N 35/00871
See application file for complete search history.

(56) References Cited

U.S. PATENT DOCUMENTS 3,555,284 A    1/1971   Anderson
5,746,976 A    5/1998   Anderson
(Continued)

FOREIGN PATENT DOCUMENTS

EP    0262497       4/1988
EP    0262497 A1    4/1988
(Continued)

OTHER PUBLICATIONS

PCT/GB2014/050124 International Search Report, 2 pages, dated Jun. 27, 2014.
(Continued)

*Primary Examiner* — Kathryn Wright
(74) *Attorney, Agent, or Firm* — Vedder Price P.C.

(57) ABSTRACT

A system for conducting an assay comprises a power source (16), a controller (13) for controlling the assay and a plurality of assay units (14) operatively connected to one another such that the controller can communicate with the assay units and the system is capable of conducting the assay. An assay device comprises a substantially circular body (24) having a plurality of chambers in fluid connection such that fluid can pass between said chambers and a central hub (200) having a sample inlet (202) disposed therein for receiving a sample.

12 Claims, 12 Drawing Sheets

(51) Int. Cl.
   *G01N 35/00* (2006.01)
   *G01N 35/04* (2006.01)
   *B01L 3/00* (2006.01)
   *G01J 3/46* (2006.01)
   *G01J 5/60* (2006.01)

(52) U.S. Cl.
   CPC ................ *G01J 3/46* (2013.01); *G01J 5/605* (2013.01); *G01N 33/487* (2013.01); *G01N 35/00* (2013.01); *G01N 35/00871* (2013.01); *G01N 35/04* (2013.01); *B01L 2300/021* (2013.01); *B01L 2300/0803* (2013.01); *G01J 2003/466* (2013.01); *G01N 2021/6439* (2013.01); *G01N 2035/00158* (2013.01); *G01N 2035/00306* (2013.01); *G01N 2035/00326* (2013.01); *G01N 2035/00752* (2013.01); *G01N 2035/00821* (2013.01); *G01N 2035/00851* (2013.01); *G01N 2035/0441* (2013.01); *G01N 2201/024* (2013.01); *G01N 2201/0256* (2013.01); *G01N 2201/0407* (2013.01)

(56) References Cited

U.S. PATENT DOCUMENTS

| | | | |
|---|---|---|---|
| 5,928,952 A * | 7/1999 | Hutchins | B01J 19/004 422/561 |
| 6,066,243 A | 5/2000 | Anderson et al. | |
| 2002/0118355 A1* | 8/2002 | Worthington | G01N 35/00069 356/72 |
| 2008/0233653 A1 | 9/2008 | Hess et al. | |
| 2009/0293643 A1* | 12/2009 | Powell | B01L 9/543 73/863.01 |
| 2010/0120129 A1 | 5/2010 | Amshey et al. | |
| 2013/0078624 A1* | 3/2013 | Holmes | C12Q 1/00 435/6.11 |

FOREIGN PATENT DOCUMENTS

| | | | |
|---|---|---|---|
| EP | 0626711 A1 * | 11/1994 | ......... H01H 71/0271 |
| EP | 2241893 | 10/2010 | |
| EP | 2241893 A2 | 10/2010 | |
| EP | 2277624 | 1/2011 | |
| EP | 2277624 A2 | 1/2011 | |
| EP | 2447702 | 5/2012 | |
| EP | 2455762 | 5/2012 | |
| EP | 2455762 A1 | 5/2012 | |
| WO | 0220160 A1 | 3/2002 | |
| WO | WO 02/20160 | 3/2002 | |
| WO | 2005016527 A2 | 2/2005 | |
| WO | WO 2005/016527 | 2/2005 | |
| WO | WO2009/026339 | 2/2009 | |
| WO | WO2010/048631 | 4/2010 | |

OTHER PUBLICATIONS

GB1300813.1 Search Report, 1 page, dated Jun. 4, 2013.
International Search Report filed in PCT/GB2014/050124; dated Jun. 27, 2014; 3 pgs.

* cited by examiner

| READABLE CHARACTERS | NUMBER OF CHARACTERS |
|---|---|
| 0-9 | 10 |
| A-Z | 26 |
| a-z | 26 |
| !"£$%^&*()_+-={}[]:;@'~#<,>.?/¬' | 32 |
| TOTAL CHARACTERS: | 94 |

COLOUR CODE:
BRWRORCBGCYCGCRPYGRPYPBGGYCYBBPWOYRPRPRWR

MODULAR ASSAY SYSTEM

The present invention relates to a modular assay system.

In remote areas or even point of care analysis of biological samples is difficult for a number of reasons. Most often, the assay devices required for processing complex assays or processing high volumes of samples are so large that it is not possible to provide the device in the area in which the sample is obtained from a patient and as such the service cannot be provided in a timely manner. Samples must be sent to laboratories having the space and access to large assay devices.

It would be beneficial to have a robust assay device that can be portable and provide point of care assaying of biological samples and which has the versatility to be up-scaled for high through put biological assaying.

In accordance with a first aspect of the present invention there is provided a system for conducting an assay comprising a power source, a controller for controlling the assay and a plurality of assay units operatively connected to one another such that the controller can communicate with the assay units and the system is capable of conducting the assay.

In one embodiment each assay unit has means for operatively connecting to another unit.

In another embodiment the means for operatively connecting to another unit comprises one member of a mating pair. In another embodiment the mating pair comprises a plug and socket. The mating pair may allow for vertical connection between adjacent units.

In another embodiment a plurality of assay units arranged in towers, with adjacent units mounted one on top of another.

A plurality of towers may be operatively connected to one another.

In another embodiment the system may comprise a controller in the form of a control unit.

In another embodiment each assay unit comprises locating means for locating said unit \n a docked configuration with another assay unit. The locating means may comprise a first member on a first unit and a second member on a second unit.

The first and second members may each comprise one of the following: a locating arm or a stop lug.

In another embodiment the first member comprises a locating arm and the second member comprises a stop lug. Each assay unit may comprise both a locating arm and a stop lug such that it is able to connect to two other discrete units.

In another embodiment each unit comprises a plurality of first and second locating members.

In another embodiment the system may comprise securing means for securing units together. The securing means may comprise a first member disposed on a first unit and a second member disposed on a second unit. The first member of the securing means may comprise a tab and the second member may comprise a complementarity shaped recess. The securing means may additionally comprise a threaded fastener which passes through an aperture in the tab and complementarily shaped recess.

In another embodiment, located within each assay unit is heating means for subjecting a sample and/or reagents to localised heat. Localised heat is achieved by means of induction and/or resistive heating means.

Preferably, localised heat is by means of induction with said means located within the assay unit.

The application of heat can be applied at various sites on the assay device. This can be achieved through control of the rotation of the assay device within each unit such that different regions of the assay device can be presented to the heating means as desired and as required by the particular assay being conducted.

The system may comprise more than one heating means.

The heating means may comprise a wireless induction heating system or heat transfer using resistive heating foil The assay device may comprise one or more areas or features comprising a metal.

The metal may be any one or more of nickel, iron or copper.

Preferably, the metal used is nickel. The metal may comprise the induction heating element.

The heating means may comprise means for applying an alternating magnetic field using an electromagnet through which a high-frequency alternating current (AC) is passed.

Each assay unit may comprise an optical detector for use in an assay. The optical detector may be capable of determining colour and sending appropriate signals to a controller.

The system may comprise means for determining temperature. Preferably, the means is capable of determining the temperature of a localised area within the system. More preferably, the means is capable of determining the temperature of a localised area on the assay device.

The means for determining temperature may comprise a thermochromic coating. The thermochromic coating may be applied in one or more discrete sections of the assay device. The coating may be in the form of a patch applied to the assay device.

The thermochromic coating may determine that the temperature within a specified area has reached the desired temperature {the coating will change colour within a defined temperature range). This can be detected by the system and a signal sent to the controller. The controller may then switch off the heating element. The heating element may be selectively switched on/off as directed by central control unit {identified by colour alteration in the thermochromic patch).

The thermochromic patch could also be used to locate/position the assay device in the correct orientation within the system.

The thermochromic coating may comprise any one or more of a thermochromic paint, dye paper or liquid crystals.

For controlling processes such as an assay on a disk, there are several known possibilities to stop or let liquids pass again at controlled points and at controlled times. One example is generating a local hydrophobization, as described in M. Madou et al., "Lab on a CD, *Annual Review of Biomedical Engineering*, Vol. 8, p. 601-628, 2006. C. T. Schembri et al., "Centrifugation and Capillarity Integrated Into A Multiple Analyte Whole-Blood Analyzer", *Journal of Automatic Chemistry*, Vol. 17, No. 3, p. 99-104, May 1995 discloses filling of a siphon-shaped structure is suppressed by an adverse centrifugal field. If the rotational frequency drops below a certain threshold the siphon is filled capillarily, and the leading meniscus may sink radially outside the liquid level in the upstream reservoir. A higher rotational speed then subsequently conveys the liquid further.

Apart from the basically reusable valves mentioned, there also exist so-called sacrificial valves, which cannot be used again after a single actuation. One example of such valves is barriers of wax or thin foils in the flow channel, which are melted by a laser and thus allow for the flow—see Y. K. Cho et al., "One-step pathogen specific DNA extraction from whole blood on a centrifugal microfluidic device", *Lab on a Chip*, Vol. 7, No. 5, p. 565-573, February 2007.

In accordance with a further aspect of the present invention, there is provided an assay device comprising a substantially circular body having a plurality of chambers in fluid connection such that fluid can pass between said chambers and a central hub having a sample inlet disposed therein for receiving a sample.

In one embodiment, the assay device has a substantially planar circular body.

In a further embodiment the assay device comprises a unique serial identifier.

A unique identifier for each assay device can identify the type of test or ensure that the device is not used beyond its expiry date. More importantly, the unique serial identifier may enable each sample introduced to the assay device could be uniquely Identified to prevent the risk of a mismatched result and/or the sample.

In order to achieve this, this unique identifier may be coded and attached to the assay device.

In a further embodiment the unique identifier comprises a 1D colour barcode, 20 barcode or an RFID tag.

Such systems as Microsoft's High Capacity Colour Barcode (HCCB) technology may be used.

The unique serial identifier may be physically attached to or incorporated in the assay device. The disadvantage with using a simple linear 10 barcode is that the length of the label becomes prohibitive. Other methods, such as a 20 barcode or an RFID tag, can be used. A 2D barcode label becomes advantageous for the higher amount of data could be stored in a 0.75"×0.75" square region. A 2D barcode could be detected by a 20 barcode scanner which uses the imaging technology. There is a minimum reading distance required to read the 20 barcode due to the optical path. In order to reduce the optical patch, additional mirror and optical components are required.

RFID could be an option for its compactness and able to store a reasonable amount information. It has one major advantage over the 1D or 20 barcode system where the content could be modified to store additional information if required. However, the cost of a RFID increases the consumable overhead cost for the small size RFID without occupied the space on the disc.

To overcome the limitation of the length of 1D barcode, a cost efficient way of achieving the same level of coding system is to utilise the same optical detector for detecting the fluorescence output to detect multiple colour patches which may be a dot or line.

Essentially colour patches are marked or printed along the circumference of the assay device. When the disc rotates each colour patch is scanned sequentially through the optical sensor to form a linear stream of data. When the assay device is rotated, each colour patch may be scanned by the optical sensor forming a linear radial colour barcode. With the multiple colour patches, a higher density of data is achieved.

Table 1 below shows the list of distinct colours that could used as the colour code with the ideal values of RGB measured by the optical sensor:

TABLE 1

| code | colour | R value | G value | B value | Discrimination (Reference R) |
|---|---|---|---|---|---|
| R | Red | 255 | 0 | 0 | 0 |
| 0 | Orange | 255 | 128 | 0 | 128 |
| Y | Yellow | 255 | 255 | 0 | 255 |
| G | Green | 0 | 255 | 0 | 2S5 |
| C | Cyan | 0 | 255 | 255 | 255 |
| B | Blue | 0 | 0 | 255 | 255 |
| P | Pink | 255 | 0 | 255 | 255 |
| W | White | 255 | 255 | 255 | 512 |

TABLE 1-continued

Table 1 shows the ideal RGB values required to be measured by the optical sensor. In real application, the colours should be carefully chosen such that minimum colour discrimination of 128 could be achieved. For example, if R, G and B on the table above are used 1 the minimum colour discrimination for each colour is 256.

FIG. 11 shows the 94 readable characters that can be encoded with colour codes:

In one embodiment, using 3 types of colour patches (R, G, B) a combination of 4 patches is required to represent the 94 readable characters while 3 patches are required for each readable character.

For example, a string of 20 characters would require 4×20 (80) patches using 3 colour types patches while 3×20 (60) patches by using 8 colour types patches.

In order to further improve the data density, each character could be converted into binary and then encodes using the table below:

| Binary | Code | Colour |
|---|---|---|
| 000 | R | Red |
| 001 | O | Orange |
| 010 | Y | Yellow |
| 011 | G | Green |
| 100 | C | Cyan |
| 101 | B | Blue |
| 110 | P | Pink |
| 111 | W | White |

For example, the string "ABCD241212CODELOT ###" when converted into binary is
"100000110000101000011100010011001011010 0110-001110010110001110010
10000111001111100010010001011001100100111 11010-100100011100011100 0110000000"

By encoding using 3 binary digits, the encoded string becomes: "BRWRORCBGCYCGCRPYCRPYGRPYPBG-GYCYBBPWOYRPRPRW R"

which reduces the number of colour patches to 45. An example is shown in FIG. 12.

A number of means for formatting the colour patches are envisaged. Two such methods of formatting the colour patches are described below:

i. Continuous
ii. Alternate with a blank patch.

In Continuous mode, the colour patches are arranged such that the colours are very closed to each other to such that a continuous optical signal is measured by the optical sensor. The advantage of this format is the length of the codes is significantly reduced. However, size of the patch needs to be selected such that it is at least double the size of the minimum rotational angle of the stepper motor. This is to prevent any patches are missed out during reading. In this mode, each patches needs to be positioned on top of the optical sensor and stepped through sequentially. This could make the system to lose the accuracy of the reading if the patch does not align to the sensor. To improve this, the second method is introduced.

In second mode, a blank patch is inserted in between two colour patches. This blank patch (black) when read by the optical sensor produced a low signal. This acts as the sampling notch indicating a valid data is located in between the two sampling notch. This method will improve the accuracy of reading as we know the position of valid data. However, the length of code is double in size.

The instrument may use a recipe system that could be used to reprogram the device to perform, a test. The recipe contains the information about the set of parameters and conditions that are used to configure the system to run a particular test. Usually this recipe information could be printed in a sheet of paper in barcode and the information is scanned and stored in the instrument as a new recipe or replacing the existing recipe. This method reduces the hassle of setting the parameters for the new disc, more intuitive as the user needs only very basic instruction to utilise the system. This prevents transcription errors that could ruin the testing if the settings do not programme correctly On the other hand, if this recipe information could be put on the disc, the instrument could automatically download the recipe from the disc and the new type of disc could be used instantaneously further reducing the step required to setting up the new discs. If the recipe needs updating, it could automatically replace the old recipe and prevents a user from using the old testing parameters accidentally.

In one embodiment, the colour coding itself may contain a low level of security where it is tailored made to the response of the optical detection unit and the colour code patterns are fairly hard to recognise. However, without any encryption, there is a chance that the content could be extracted. The recipe information is the key for the instrument to operate. We do not want user to mess around with the settings that potentially invalidate the test results. The encryption could be performed easily in this colour coding system. The most straight forward method is to scramble the mapping of the colour code with the binary data using a key. This key will be used for the decryption process.

In one embodiment, the barcode is printed using UV sensitive ink such that the barcode is not visible to the human eye but can be read using suitable detection devices.

Each assay unit may comprise an optical detector for use in an assay. In one embodiment, the same optical detector may be used to read the barcode and, for example, to subsequently detect the fluorescence output from the assay.

The following examples illustrate specific embodiments of the present invention, by way of example only, as follows:

FIGS. 1*a* and *b* show a system in accordance with the present invention;

FIG. 2 shows a tower unit in accordance with the present invention;

FIGS. 3*a* and *b* show the housing and connectors of an assay unit in accordance with the present invention;

FIGS. 4*a* and *b* show two assay units connected to one another in accordance with the present invention;

Figure 1A:
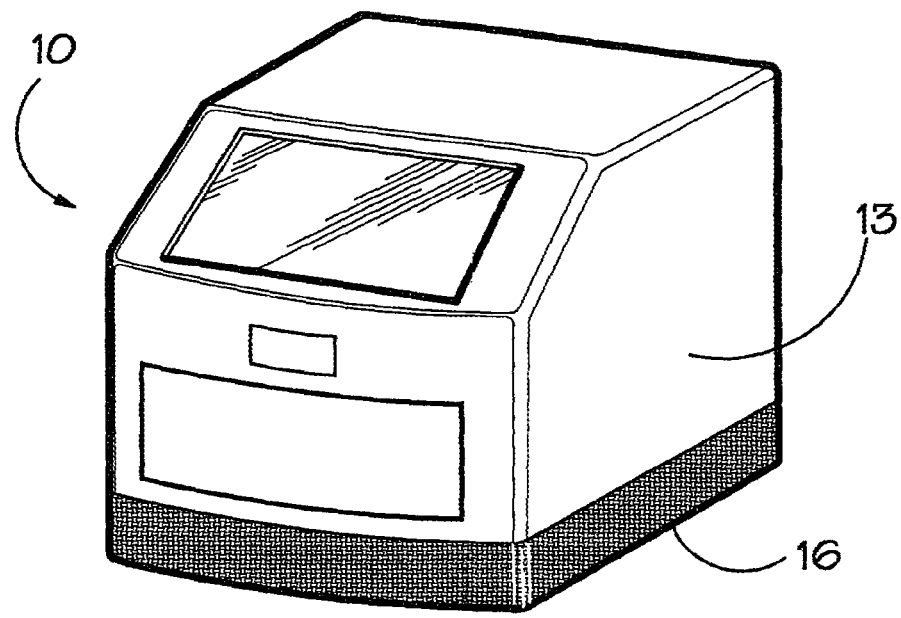
Figure 1B:
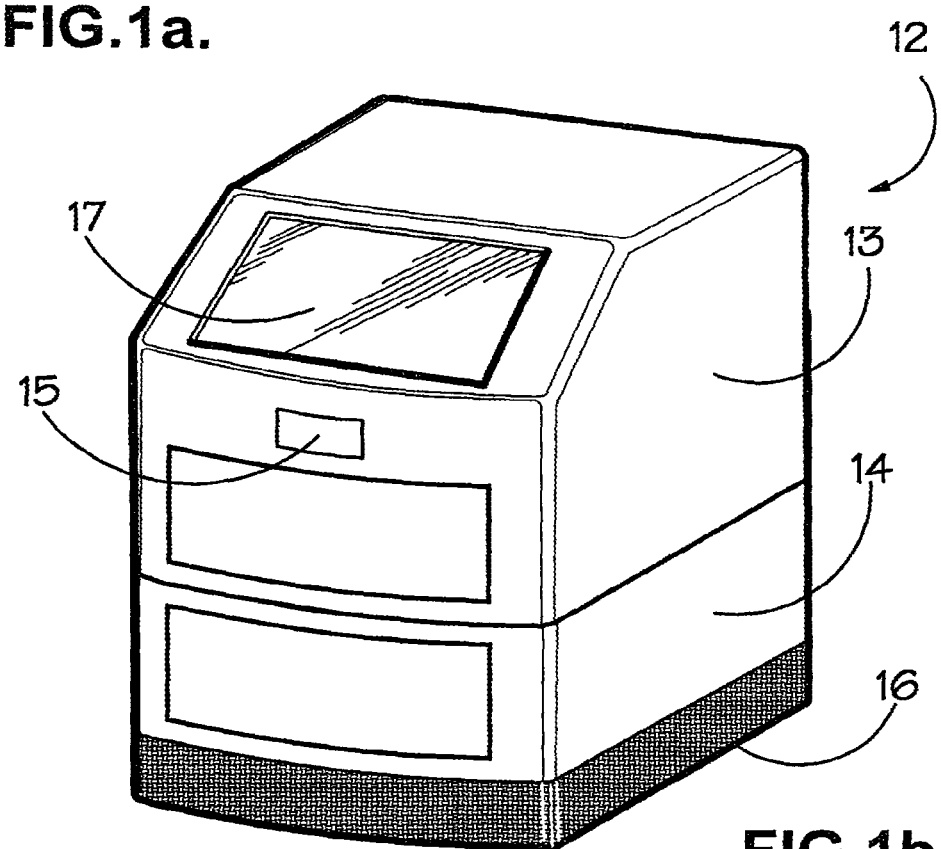

FIG. 1*a* shows a basic system 10 comprising a control unit 13 and a battery unit 16. FIG. 1*b* shows a system 10 comprising a tower 12 consisting of a control unit 13, a discrete assay unit 14 mounted on a power unit 16. Located in control unit 13 is a bar code reader 15 and a touch screen interface 17 for a user to interact with the control unit 13. The bar code reader is capable of reading a bar code located on an assay device for use in the system.

Figure 2:
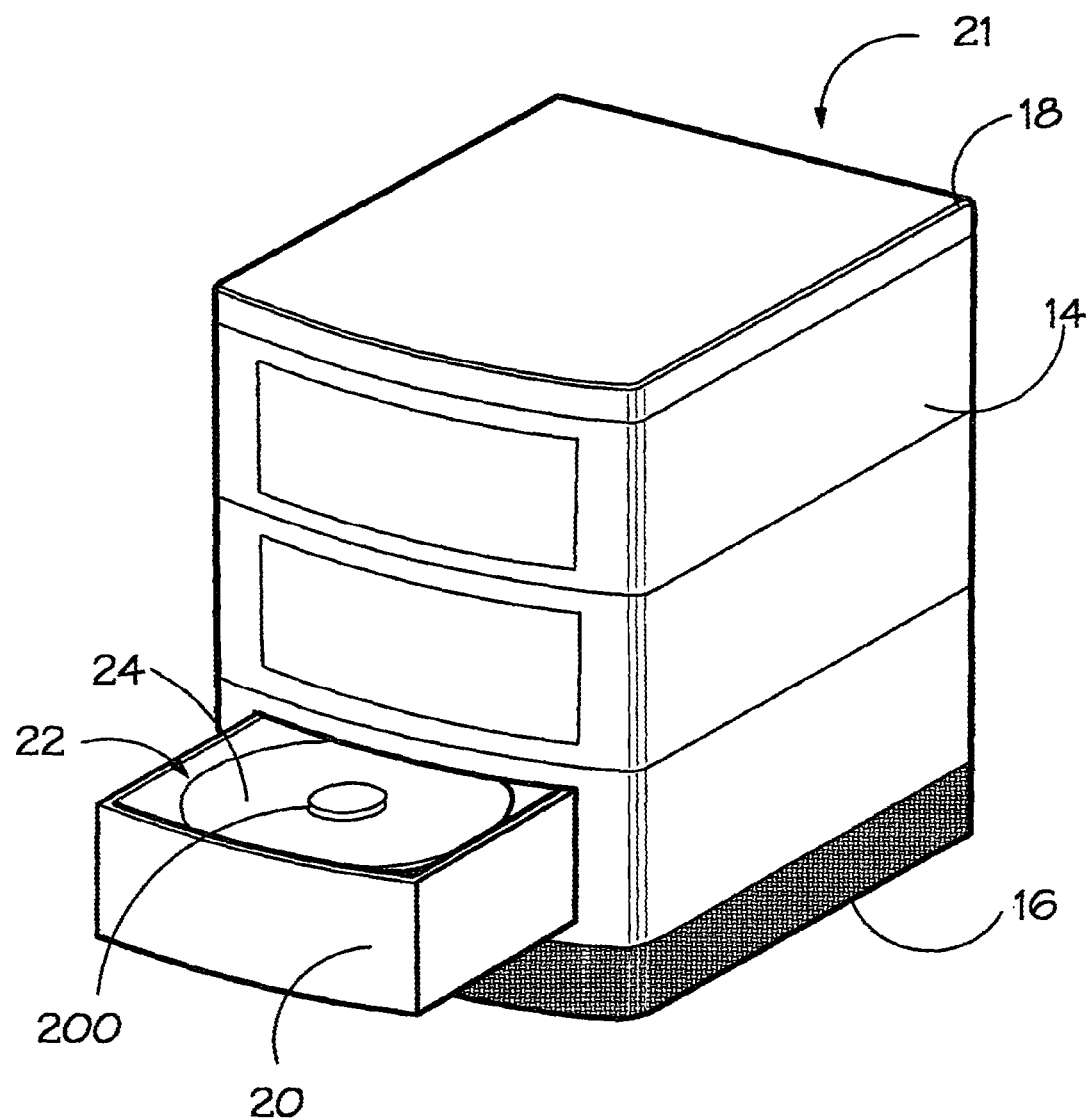
Figure 3A:
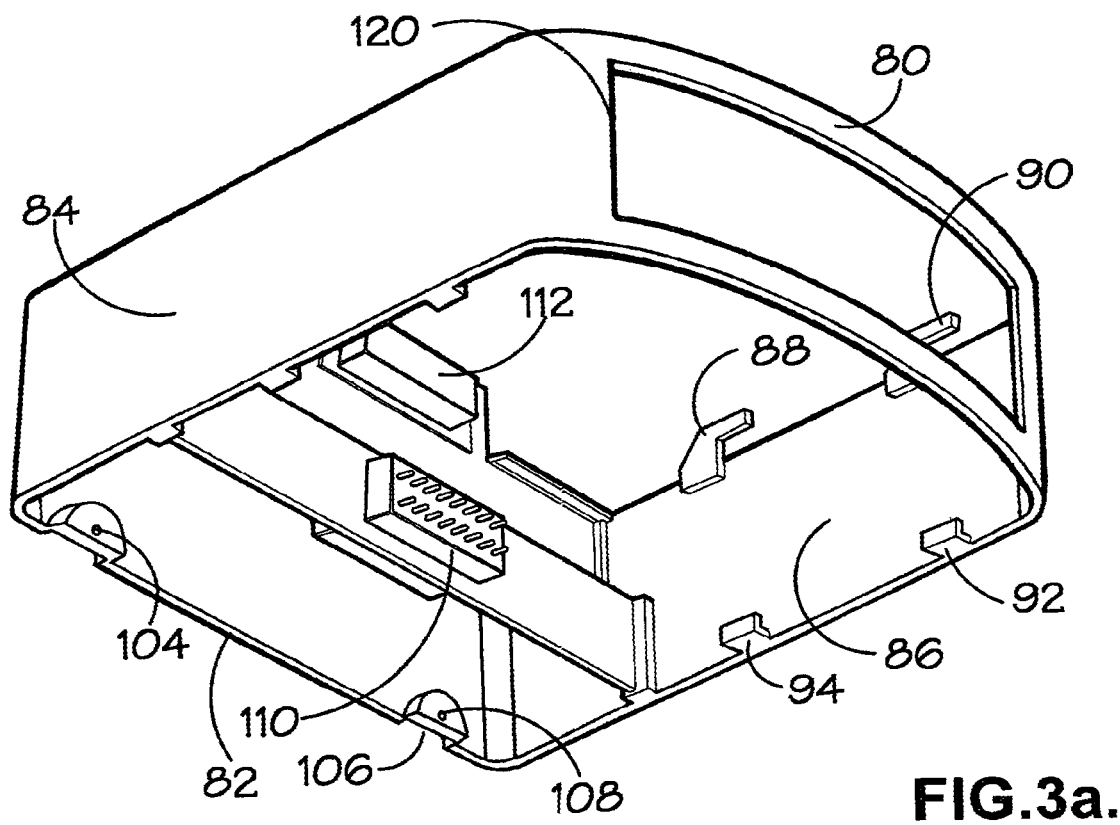
Figure 3B:
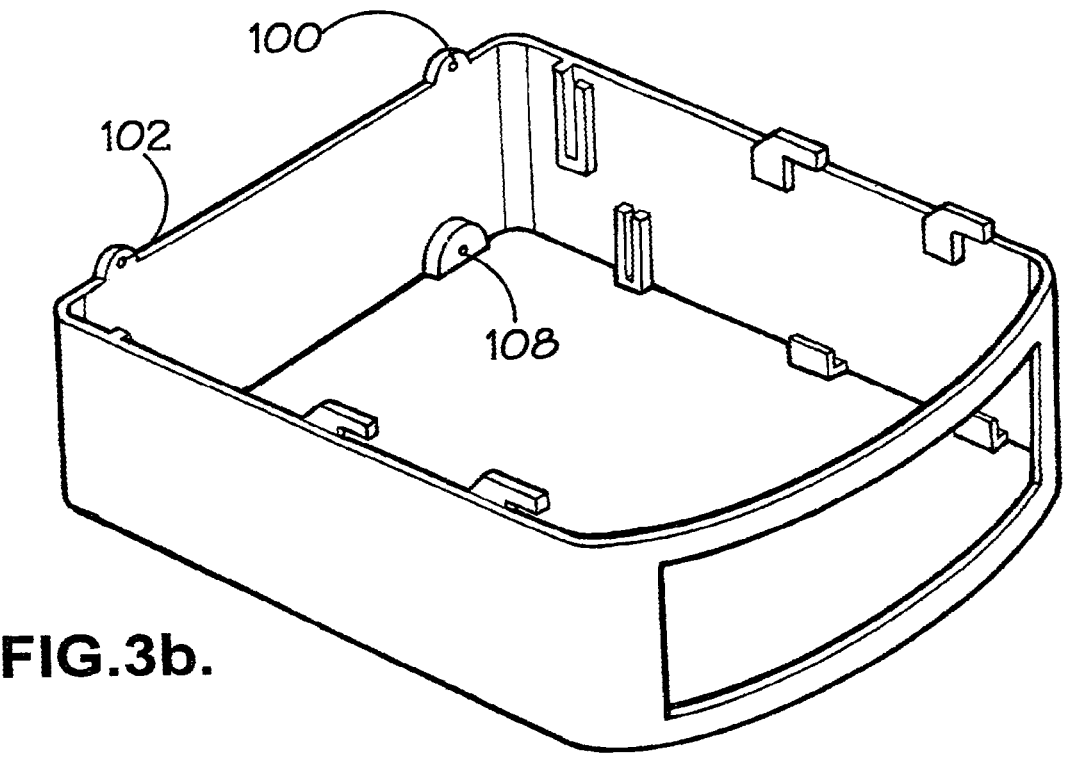

FIG. 2 shows a tower unit 21 comprising a number of discrete assay units 14 and a power source in the form of a battery unit 16 connected to an assay unit.

In this embodiment, the control unit comprises a touch sensitive screen which is angularly disposed with respect to a user for ease of use and reading the screen in bright light conditions. In an alternative embodiment, the screen can be pivotally mounted on the control unit such that it can be moved about it's pivot for ease of operation, for example, to avoid reflection issues in bright sunlight. Located in an open drawer 20 of the bottom assay unit 14 is an assay device 22 having a disc body 24 and a central hub 200. The assay device is received by a motor shaft which is capable of rotating the assay device according to signals sent by the controller of the control unit.

The battery unit 16 comprises one DC connector 74 (12V DC in) and two "signal" sockets, 9-way D-type, 70,72, for example. A higher voltage can be used, typically 12-50 V.

Each unit is substantially rectangular, having a front 80 and rear 82 wall and two side walls 84,86.

Disposed on each side wall is a pair of locating arms 88,90 and two stop lugs 92,94. The locating arms 88,90 are disposed on the upper edge of each side wan and the stop lugs 92,94 are located on the lower edge of each sidewall and extend perpendicularly with respect to the plane of each sidewall such that the stop lugs do not extend beyond the bottom edge of each side wall. In contrast the locating arms extend above the upper edge of each side wall. The locating arms have a substantially L-shape, one end being integrally formed with the sidewall whilst the free end extend in a direction parallel to that of the upper edge of the side wall.

Located on the upper edge of the rear wall of each unit are two securing tabs 100, 102. Disposed on the lower edge of rear wall 82 are two recesses 104,106 complementarily shaped with respect to tabs 100,102. Securing tabs 100,102 are received by recesses 104,106 of an adjacent unit when located. The tabs and recesses each have an aperture 108 which, when aligned form a through going bore through which a fastener can pass securing adjacent units in a docked position.

To operatively connect adjacent assay units, a horizontal mating plug 110 and socket 112 is employed. Each unit has a socket to mate with a second unit and a plug to mate with a third unit. Typically, the plug is arranged to engage and mate with a unit disposed below the unit whilst the socket Is arranged to engage and mate with a unit disposed above the unit in question.

To assemble a tower one unit is docked with another.

Figure 4A:
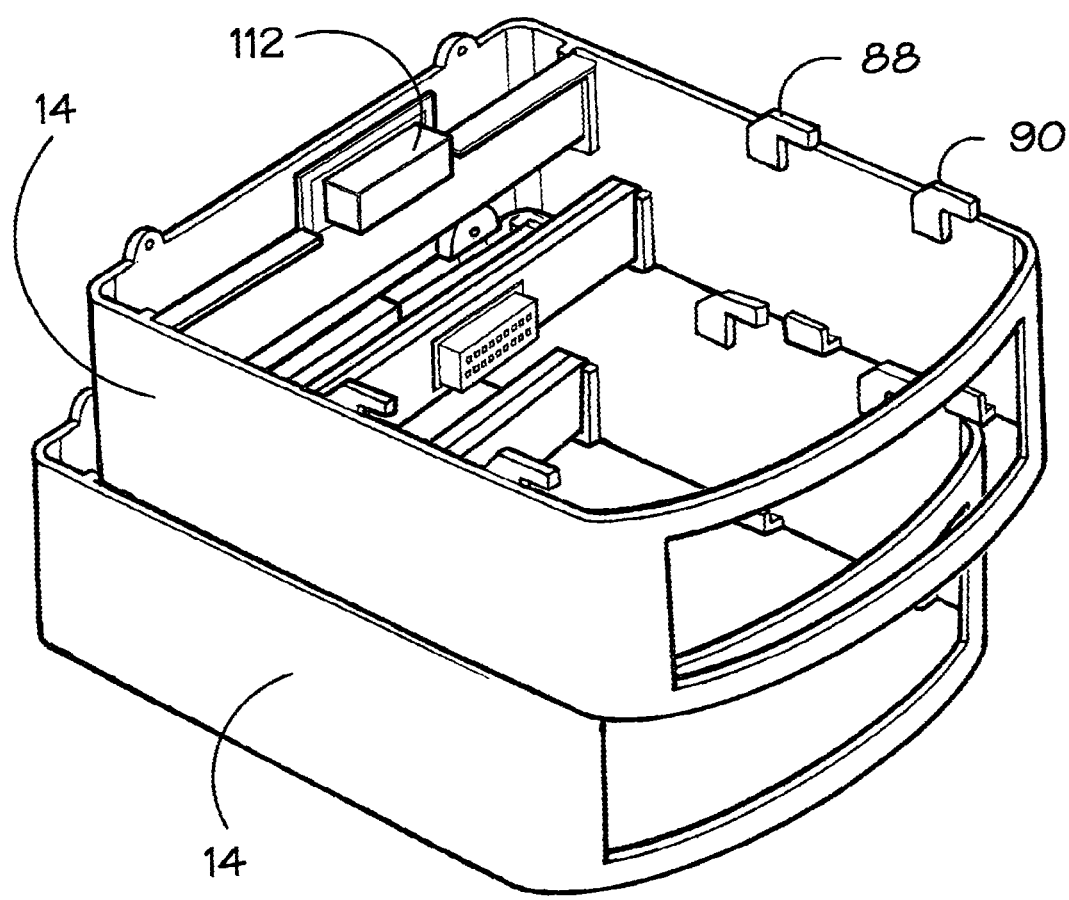
Figure 4B:
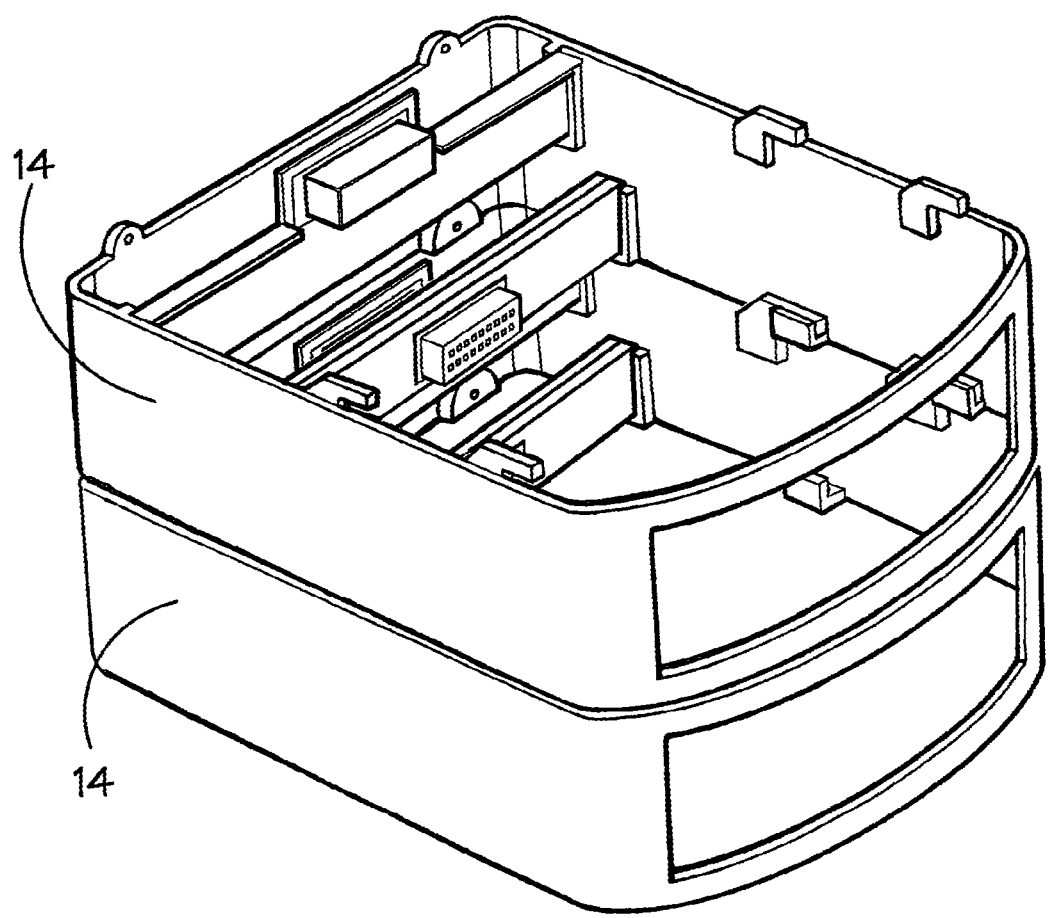

A second unit is docked with a second unit by sliding the second unit (see FIGS. 4*a* and *b*) into position on top of the first unit. In so doing, plug 1112 can mate with socket 110. Locating arms 88,90 can engage with stop lugs 92,94 and securing tabs 100,102 can be received by recesses 104,106.

To firmly secure the units in the docked configuration two fasteners (screws) can be used to secure the units.

Each unit is operatively connected via plug 110 and socket 112 to the other such that they can communicate with and through each other.

The front wall 80 of each assay unit has an opening 120 for receiving a drawer 20 which itself is arranged to receive an assay device 24. The assay device is a substantially planar disc in shape having a central hub around which is disposed assay chambers capable of containing reagents, connected to one another by capillaries.

Each drawer can be selectively opened and closed as necessary. The main control unit is capable of sending a command to any one or more assay units in the system to selectively open or close the drawer, or indicate which assay unit or units are to be used, as required. When an assay is to be carried out, an assay device 24 is loaded with a sample and placed in the assay drawer in its open configuration. The control unit is then used to initiate the assay programme and the drawer moves to its closed configuration, thus moving the disc within the assay unit to conduct the assay in accordance with the programmed instructions stored in the control unit.

All interconnections within a tower between units are made automatically when a new unit is slid into position. The signals between each drive bay and the main control unit on the top of the first tower can all connect to a parallel "bus" so, by fitting two sockets to the rear of the battery unit, users can connect one or more additional towers (without control units) in the most convenient way. For example, two additional towers positioned either side of the "control" tower can each be connected to the closest socket on the battery unit. It does not matter which socket is used on the additional units. If the additional units are both placed on the same side of the control unit, one cable can connect from a socket on the battery unit to a socket on the first additional unit and a second cable can be plugged into its second socket and routed to the second additional unit. A third tower could be connected, in a similar manner, to the second tower.

The connections from this signal bus and the dc supply connections will be fed to the assay units using Flexible Printed Circuit strips and appropriate connectors (not shown).

Figure 5:
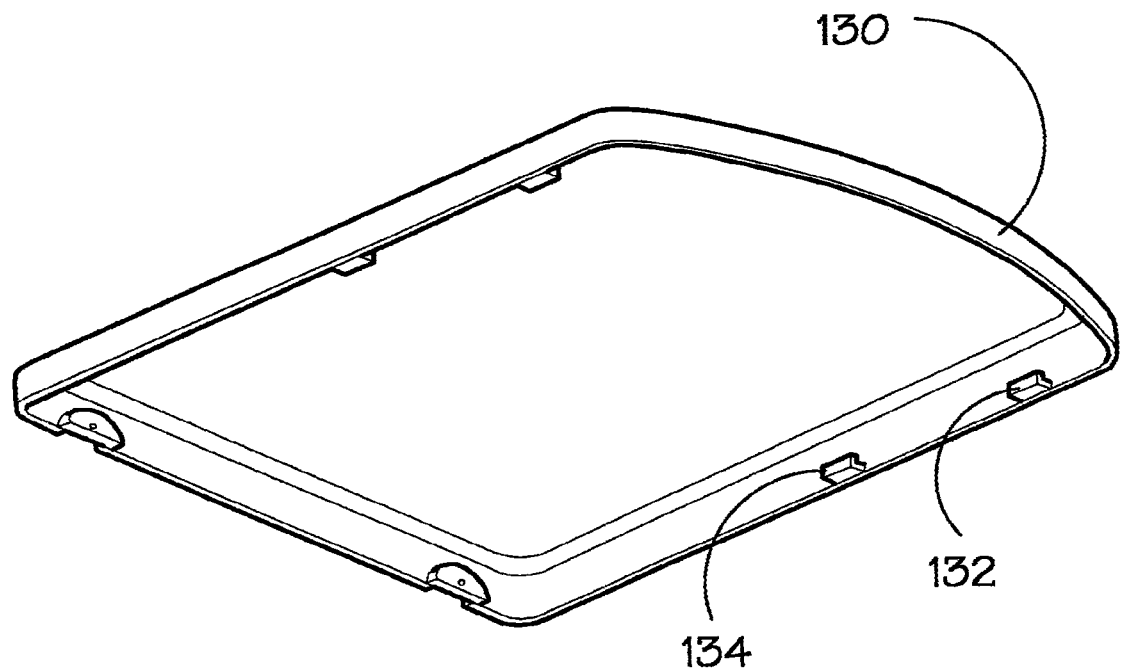
FIG. 5 shows a lid for use in a system in accordance with the present invention.
Figure 6:
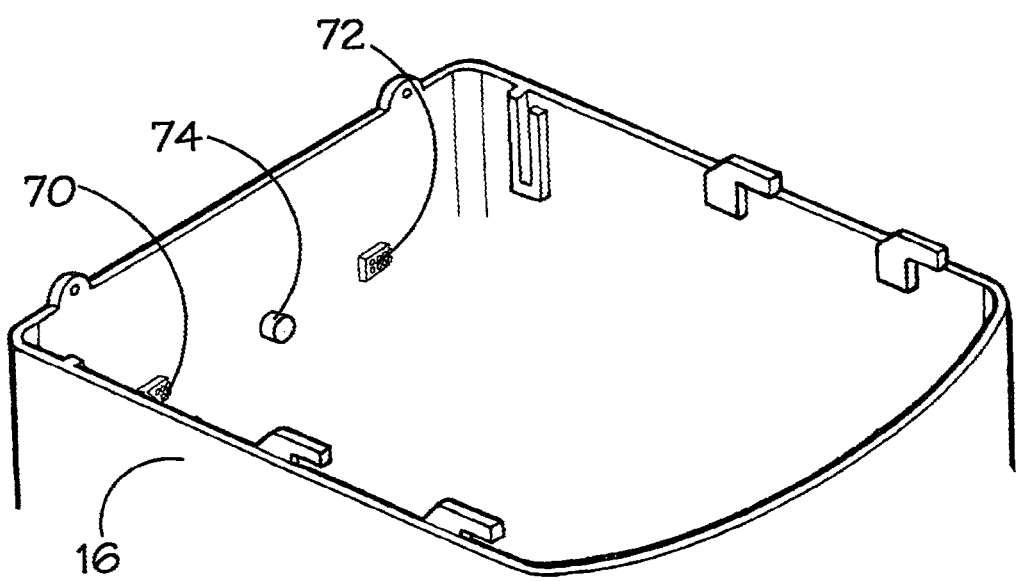
FIG. 6 shows a battery unit in accordance with the present invention.

FIG. 5 shows a lid 130 which is used as the top section of a tower that does not have a control unit. The lid seals the unit below from the surrounding environment. Each lid comprises two stop lugs 132,134 on each side wall and two securing recesses 136,138 which engage with the locating arms and securing tabs respectively of the unit below.

The control unit fits to the top drive bay in the same manner as other drive bays but does not require a lid. To simplify internal wiring, any additional ports, e.g. USB or Network will be mounted on the Control Unit.

In an alternative embodiment, the control unit has a screen in a fixed position which is ergonomically disposed with respect to a user during use.

Figure 7:
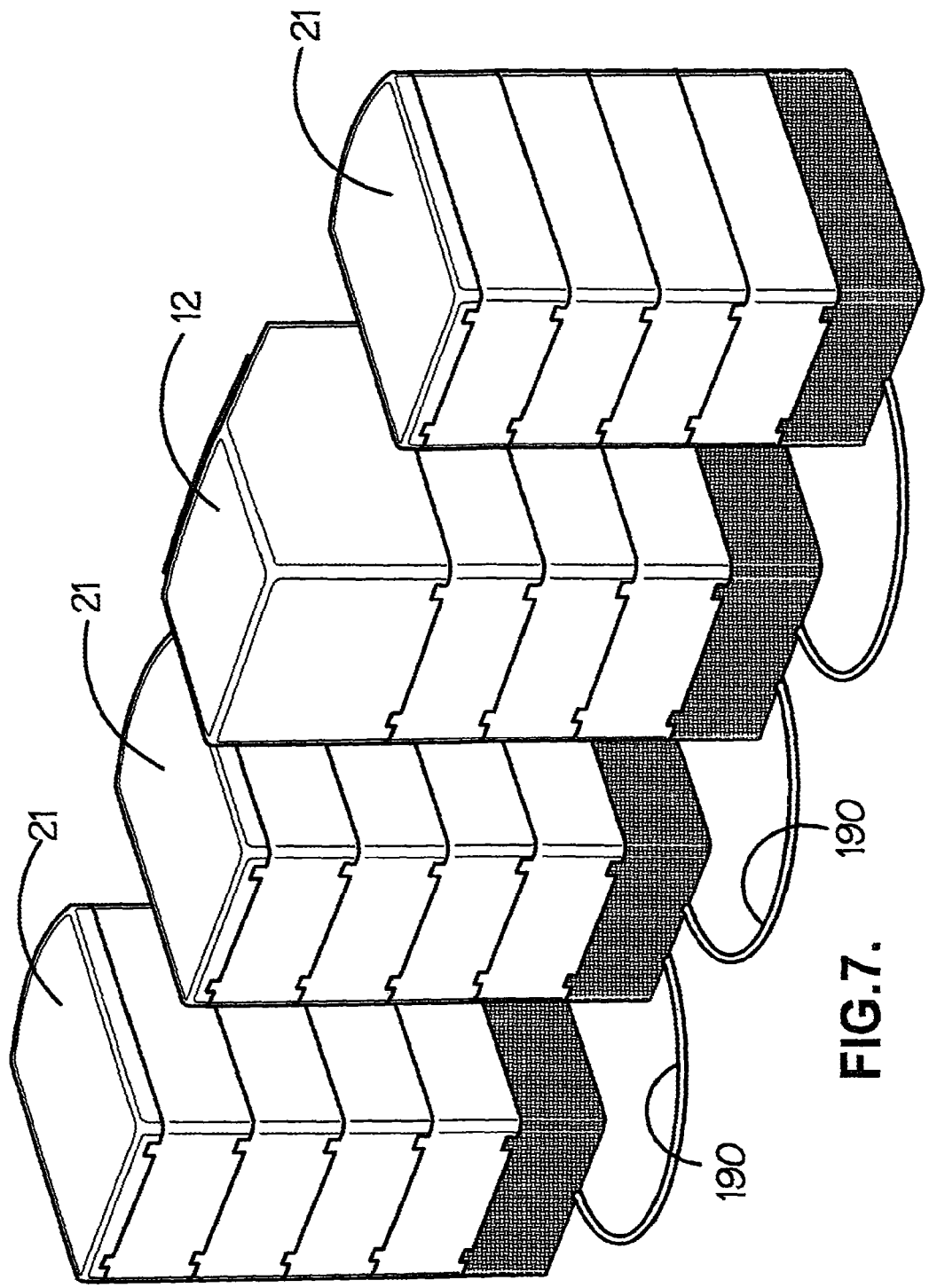
FIG. 7 shows a system in accordance with the present invention.

FIG. 7 shows a plurality of towers 21 connected to a main control unit tower 12. Each of the towers 21 are connected to the control unit tower either directly or via towers 12 linked in series via cabling 190.

Figure 8:
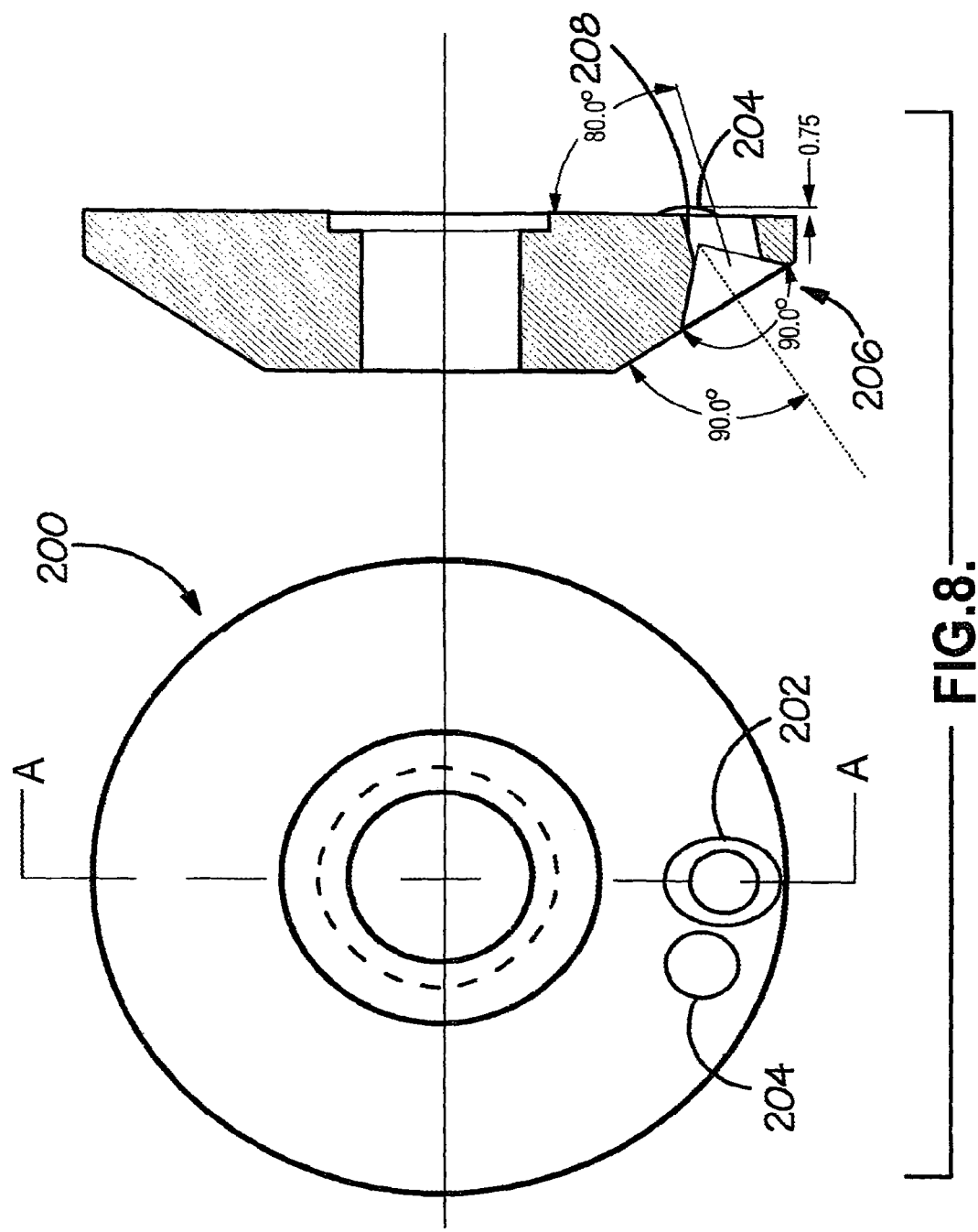
FIG. 8 shows a central hub of an assay device in accordance with the present invention.
Figure 9:
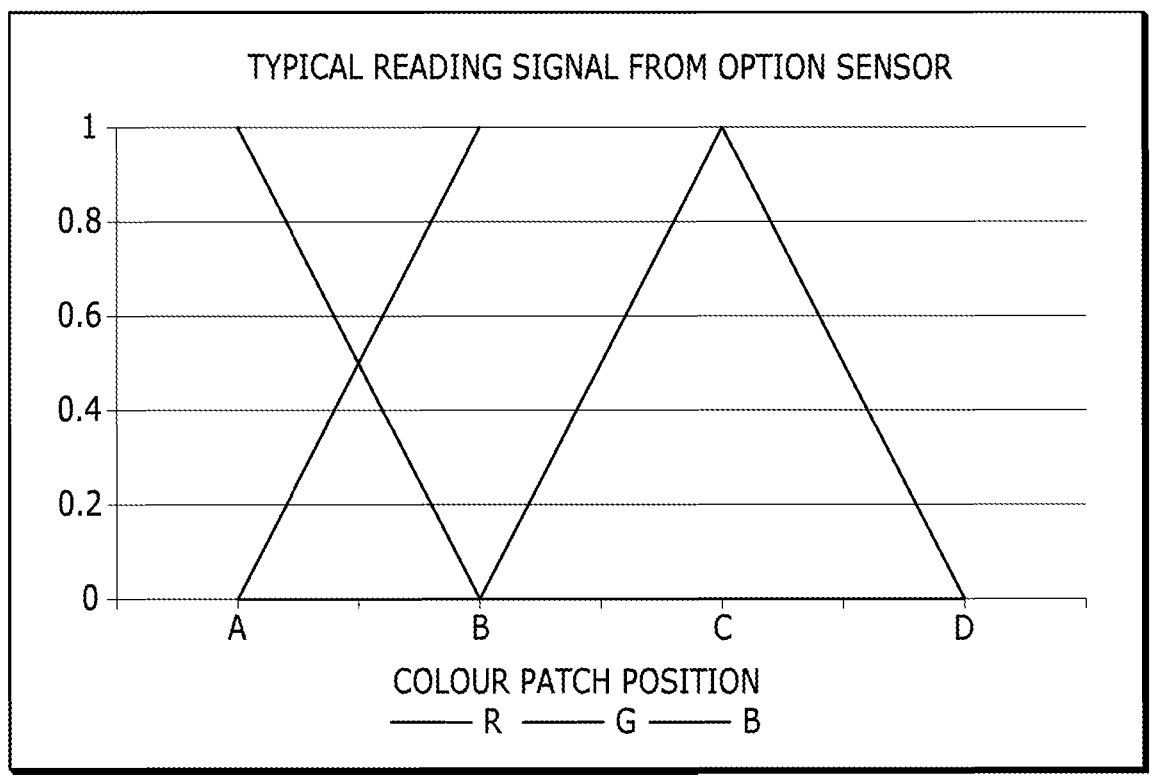
FIGS. 9 and 10 show typical reading signal from Optical sensor in an embodiment of the present invention.
Figure 10:
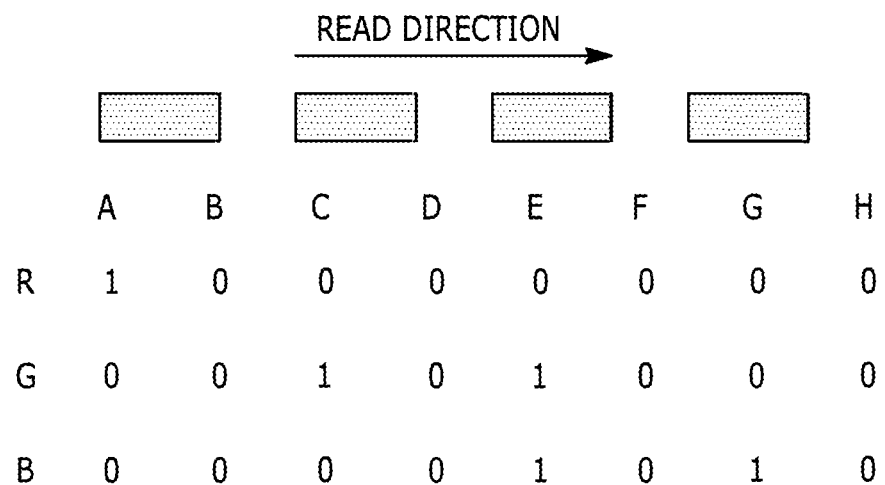
Figure 10:
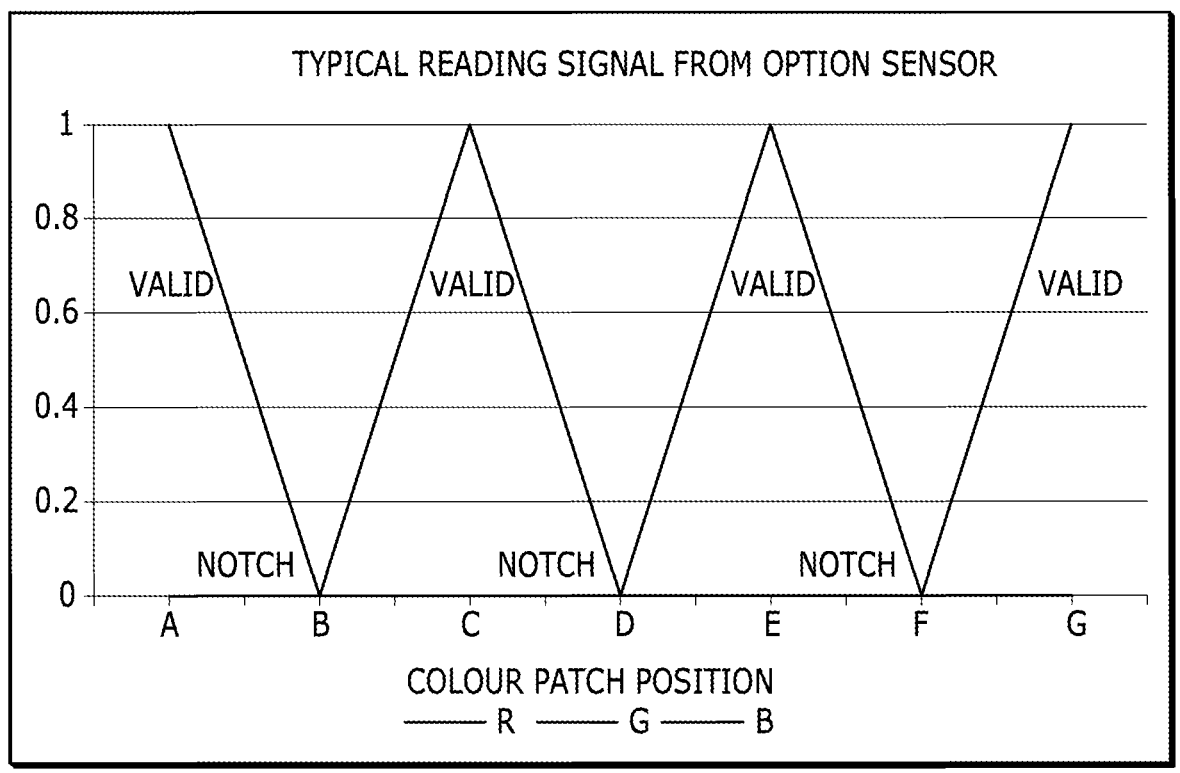
Figures 11, 12:
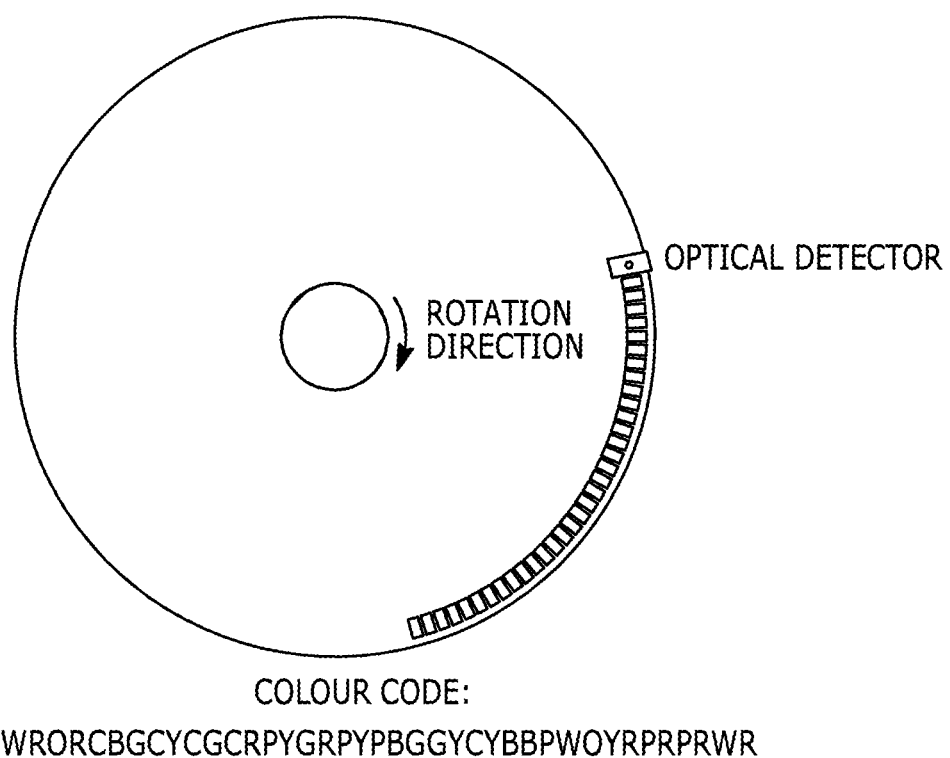
FIG. 11 shows the coding in an embodiment of the present invention.
FIG. 12 shows an example of an encoded string formed by encoding 3 binary digits in an embodiment of the present invention.
Figure 13:
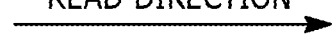
FIG. 13 shows a typical reading signal from the Optical Sensor in an embodiment of the present invention.

FIG. 8 shows a central hub 200 of an assay device in accordance with an embodiment of the present invention. The hub is centrally mounted on a disc shaped assay device (not shown). Located near to its circumference is a sample inlet 202 and adjacent to that is a nipple 204. Inlet 202 comprises a through going bore 206 having a side wan 208. The sample inlet 202 is in a first configuration aligned with and in fluid communication with a sample inlet (not shown) located on the disc portion of the assay device such that fluid can flow from the inlet 202 into the disc portion of the assay device. Once a sample has been introduced, the central hub 200 can be rotated relative to the disc and Its inlet. In so doing, the nipple or closure means, is rotated into alignment with the inlet of the disc thus sealing the sample within the disc from the surrounding environment and preventing contamination of the sample and assay reagents.

The sample inlet is shaped so as to make it relatively easy for a user to load a sample into the assay device. The sample is typically a liquid which can be introduced to the assay device via the sample inlet 202.

The invention claimed is:

1. An apparatus for conducting multiple assays comprising:
   a power source;
   a controller configured to control the assay and a plurality of individual assay units operatively connected to one another,
   the plurality of assay devices having one or more discrete sections, wherein each of the plurality of assay units is configured to load with a sample to be assayed, and each of which carries an identifier to indicate one or more of the following items of information: the type of assay or test to be carried out; or the recipe information or parameters to be followed in carrying out a test; or identifying information about the sample; or other instructions;
   the plurality of discrete assay units operatively connected to each other, each assay unit comprising a heating means configured to heat the one or more discrete sections of the assay device and a means for determining temperature comprising a thermochromic coating in one or more of the discrete sections of the assay device such that a change of the color of the one or more discrete sections signals to the controller that the temperature within a specified area has reached a certain pre-determined temperature; and
   wherein each of the plurality of discrete assay units is able to receive one of said assay devices and to move the assay device to conduct said assay,
   wherein each of said assay units comprises a drawer which can be selectively opened and closed, each of said drawers receiving a respective one of said assay devices; and
   the controller is further configured to communicate with assay units to selectively open and close the drawer of each assay unit and to control each assay independently according to information provided by each identifier,
   wherein each assay unit is operatively connected via plug and socket to another assay unit such that they can communicate with and through each other so that a plug of one assay unit mates directly and reversibly with the socket of another one of the assay units such that interconnections between assay units are made automatically when the assay units are docked with other assay units; and
   wherein the controller further comprises a plug or socket configured to mate directly and reversibly with said socket or plug of an adjacent assay unit located immediately underneath the controller when the controller is docked with said adjacent assay unit, the plugs and sockets defining a physical coupling between the assay units and between the controller and said adjacent assay unit located immediately underneath the controller through which electrical signals can be transferred between each of the assay units and the controller, respectively;

wherein the controller and each assay unit further comprise locating arms and stop lugs for locating each said assay unit in a docked configuration with an adjacent assay unit and for locating said controller in a docked configuration with said adjacent assay unit located immediately underneath the controller such that the controller and plurality of assay units comprise a stacked arrangement; and wherein the locating arms of said assay unit engage with the stop lugs of an adjacent assay unit and guide the plug and socket into a physical and electrical coupling with each other to permit transfer of electrical signals between each of the assay units and the controller during operation of the apparatus.

2. An apparatus as claimed in claim 1 wherein said assay device is an assay disc and said assay unit effects rotational movement of said assay disc to conduct said assay.

3. An apparatus as claimed in claim 1 wherein said identifier is physically attached to or incorporated in said assay device.

4. An apparatus as claimed in claim 1 wherein said identifier is a barcode or RFID tag.

5. An apparatus as claimed in claim 1 comprising means for reading said identifier and for relaying said information to said controller.

6. An apparatus as claimed in claim 1 wherein each assay unit comprises an optical detector for use in an assay.

7. An apparatus as claimed in claim 1 wherein the plurality of assay units are arranged in one or more towers, with adjacent units mounted one on top of another.

8. An apparatus as claimed in claim 6, wherein said optical detector is capable of reading a fluorescent output from an assay or capable of detecting red, green or blue colour.

9. An apparatus as claimed in claim 1, comprising the power source at the base of said stack of assay units.

10. An apparatus as claimed in claim 1, wherein the plurality of discrete assay units are arranged in a plurality of towers, each tower comprising a plurality of said discrete assay units stacked vertically with respect to one another and wherein the towers are operatively connected to one another.

11. An apparatus as claimed in claim 10, wherein said controller is mounted on top of one of said towers.

12. An apparatus as claimed in claim 1, wherein the thermochromic coating comprises one of a thermochromic paint, dye paper or liquid crystals.

* * * * *